US007218706B2

(12) United States Patent
Hopkins et al.

(10) Patent No.: US 7,218,706 B2
(45) Date of Patent: May 15, 2007

(54) ENERGY DISCRIMINATION RADIOGRAPHY SYSTEMS AND METHODS FOR INSPECTING INDUSTRIAL COMPONENTS

(75) Inventors: Forrest Frank Hopkins, Scotia, NY (US); Walter Vincent Dixon, Delanson, NY (US); Clifford Bueno, Clifton Park, NY (US); Yanfeng Du, Rexford, NY (US); Gregory Alan Mohr, West Chester, OH (US); Paul Francis Fitzgerald, Schenectady, NY (US); Thomas William Birdwell, Middleton, OH (US)

(73) Assignee: General Electric Company, Niskayuna, NY (US)

( * ) Notice: Subject to any disclaimer, the term of this patent is extended or adjusted under 35 U.S.C. 154(b) by 174 days.

(21) Appl. No.: 11/018,175

(22) Filed: Dec. 20, 2004

(65) Prior Publication Data

US 2006/0133563 A1    Jun. 22, 2006

(51) Int. Cl.
*H05G 1/64* (2006.01)
(52) U.S. Cl. .................................... 378/98.9; 378/53
(58) Field of Classification Search ................ 378/53, 378/58, 98.9, 98.11
See application file for complete search history.

(56) References Cited

U.S. PATENT DOCUMENTS

| 3,418,467 A | 12/1968 | Spielberg et al. | ............ | 378/119 |
| 4,287,416 A | 9/1981 | Kramer et al. | ............... | 250/273 |
| 4,428,902 A | 1/1984 | Murray | ........................ | 376/156 |
| 4,668,867 A | 5/1987 | Lingenfelter | ............. | 250/358.1 |
| 5,175,756 A | 12/1992 | Pongratz et al. | ............... | 378/88 |
| 5,251,240 A | 10/1993 | Grodzins | ..................... | 376/157 |
| 5,420,905 A | 5/1995 | Bertozzi | ....................... | 378/88 |

(Continued)

FOREIGN PATENT DOCUMENTS

EP    0478406    9/1993

(Continued)

OTHER PUBLICATIONS

Elizabeth L. Dixon et al., "Method of Real-Time Correction of Non-Functioning Pixels in Digital Radiography," U.S. Appl. No. 10/461,053, filed Jun. 12, 2003.

(Continued)

*Primary Examiner*—Edward J. Glick
*Assistant Examiner*—Jurie Yun
(74) *Attorney, Agent, or Firm*—Penny A. Clarke; Patrick K. Patnode (57) ABSTRACT

An energy discrimination radiography system includes at least one radiation source configured to alternately irradiate a component with radiation characterized by at least two energy spectra, where the component has a number of constituents. At least one radiation detector is configured to receive radiation passing through the component and a computer is operationally coupled to the detector. The computer is configured to receive data corresponding to each of the energy spectra for a scan of the component, process the data to generate a multi-energy data set, and decompose the multi-energy data set to generate material characterization images in substantially real time. A method for inspecting the component includes irradiating the component, receiving a data stream of energy discriminated data, processing the energy discriminated data, to generate a multi-energy data set, and decomposing the multi-energy data set, to generate material characterization images in substantially real time.

29 Claims, 6 Drawing Sheets

U.S. PATENT DOCUMENTS

| | | | |
|---|---|---|---|
| 5,712,165 A | 1/1998 | Alvarez et al. | 436/21 |
| 5,864,601 A | 1/1999 | Cattorini et al. | 378/59 |
| 6,212,253 B1 | 4/2001 | Schedel-Niedrig et al. | 378/53 |
| 6,256,372 B1 | 7/2001 | Aufrichtig et al. | 378/41 |
| 6,393,090 B1 | 5/2002 | Hsieh et al. | 378/4 |
| 6,466,643 B1 | 10/2002 | Bueno et al. | 378/58 |
| 6,470,071 B1 | 10/2002 | Baertsch et al. | 378/62 |
| 6,507,635 B2 | 1/2003 | Birdwell et al. | 378/58 |
| 6,546,075 B1 | 4/2003 | Chartier et al. | 378/98 |
| 6,614,872 B2 | 9/2003 | Bueno et al. | 378/58 |
| 6,618,465 B2 | 9/2003 | Mohr et al. | 378/58 |
| 6,823,086 B1 * | 11/2004 | Dolazza | 382/261 |
| 6,950,492 B2 * | 9/2005 | Besson | 378/5 |
| 2004/0102688 A1 | 5/2004 | Walker et al. | |

FOREIGN PATENT DOCUMENTS

| | | |
|---|---|---|
| EP | 0433171 | 3/1994 |

OTHER PUBLICATIONS

X-Ray Machines: Dynavision 6550, High Com Security Inc., Sep. 24, 2002, pp. 1-4.

* cited by examiner

ENERGY DISCRIMINATION RADIOGRAPHY SYSTEMS AND METHODS FOR INSPECTING INDUSTRIAL COMPONENTS

BACKGROUND

The invention relates generally to energy discrimination radiography for inspection of industrial components and, more particularly, to energy discrimination digital radiography for material characterization of industrial components.

Nondestructive evaluation (or testing) continues to gain prominence for the inspection of industrial components, such as turbine blades, castings, welded assemblies, and aircraft fuselage frames. The objectives of nondestructive testing include detecting, quantifying and locating inclusions and corrosion in metallic components and assessing the relative and absolute amounts of two or more materials in components of simple or generally complex geometry. Examples of such applications include determination of the amount and location of water in aluminum honeycomb, determination of the amount and location of corrosion in metallic aircraft structures, and determination of the amount and location of residual ceramic core in cast aeroengine turbine blades.

Radiographic imaging is a useful tool for the nondestructive evaluation of industrial components, such as turbine blades. However, despite recent advances in digital radiography technology, the radiographic detection of one material, particularly small amounts of that material, residing in a complex structure of another material remains problematic. Moreover, corrosion can be difficult to detect and quantify using conventional radiographic techniques. This is especially true for minor corrosion. Significant corrosion often results in reduced material in the region of interest, which in turn reduces the X-ray absorption during inspection, such that the significant corrosion can be detected using conventional radiographic inspection techniques. However, minor corrosion products can remain on the structure, and the added oxidized component of the corrosion can actually increase the absorption of X-rays during inspection. In the resulting image, the minor corrosion can appear much like an adhesive used to bond parts of the structure, thereby masking the presence of the corrosion and inhibiting its detection using conventional radiographic techniques. Other issues arise where the added X-ray absorption of the corrosion oxidizers offsets the reduction in the metal structure from lost corrosion products, making detection and quantification of the corrosion difficult using conventional radiographic techniques.

These limitations of conventional radiographic techniques stem from the fact that conventional radiographic imaging of industrial components consists of single spectrum imaging, which is limited by complex overlapped features, as well as feature shape-dependent and contrast-dependent algorithms. Consequently, material characterization of industrial components, including the detection and quantification of minor corrosion, is complicated by conventional radiographic techniques.

Accordingly, it would be desirable to provide a radiographic imaging technique with enhanced material characterization capabilities. In addition it would be desirable to provide a radiographic imaging technique for imaging complex, multi-constituent industrial components. It would further be desirable for the radiographic techniques to increase the speed of detectability, as well as the quantifiability of the amounts of different materials in an industrial component.

BRIEF DESCRIPTION

Briefly, in accordance with one embodiment of the present invention, a method for inspecting a component having a number of constituents is presented. The method includes alternately irradiating the component with radiation characterized by at least two energy spectra to scan the component, where a first one of the energy spectra is different than a second one of the energy spectra. The method further includes receiving data corresponding to each of the energy spectra, processing the data to generate a multi-energy data set, and decomposing the multi-energy data set to generate a number of material characterization images in substantially real-time.

In accordance with another embodiment of the present invention, a method for inspecting a component having a number of constituents is presented. The method includes irradiating the component, receiving a data stream corresponding to radiation passing through the component, the data comprising energy discriminated data, processing the energy discriminated data to generate a multi-energy data set, and decomposing the multi-energy data set, to generate a number of material characterization images in substantially real time.

In accordance with another embodiment of the present invention, an energy discrimination radiography system is presented. The system includes at least one radiation source configured to alternately irradiate a component with radiation characterized by at least two energy spectra, where the component has a number of constituents. The system further includes at least one radiation detector configured to receive radiation passing through the component, and a computer operationally coupled to the at least one radiation detector. The computer is configured to receive data corresponding to each of the energy spectra for a scan of the component, process the data to generate a multi-energy data set, and decompose the multi-energy data set to generate a number of material characterization images in substantially real time.

In accordance with another embodiment of the present invention, an energy discrimination radiography system is presented. An energy discrimination radiography system includes at least one radiation source configured to irradiate a component having a number of constituents. The system further includes at least one radiation detector configured to receive radiation passing through the component and to generate a data stream for a scan of the component, the data stream comprising energy discriminated data. The system further includes a computer operationally coupled to the at least one radiation detector. The computer is configured to receive the data stream, process the data stream to generate a multi-energy data set, and decompose the multi-energy data set to generate a number of material characterization images in substantially real time.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "generating an image" is not intended to exclude embodiments of the present invention in which data representing an image is generated but a viewable image is not. However, many embodiments generate (or are configured to generate) at least one viewable image.

As used herein, the phrases "multi-constituent component" or "components having a number of constituents" or the like encompass components having two or more base materials (including components intended to have two or more base materials, as well as components with a residual material, such as cast turbine blades with residual ceramic core), components having a single base material with another material located in the component (such as an aluminum honeycomb structure with water located within the structure), and components having one or more base materials with one or more of the base materials at least partially transformed, for example by aging or exposure (such as a metallic structure with corrosion).

Figure 1:
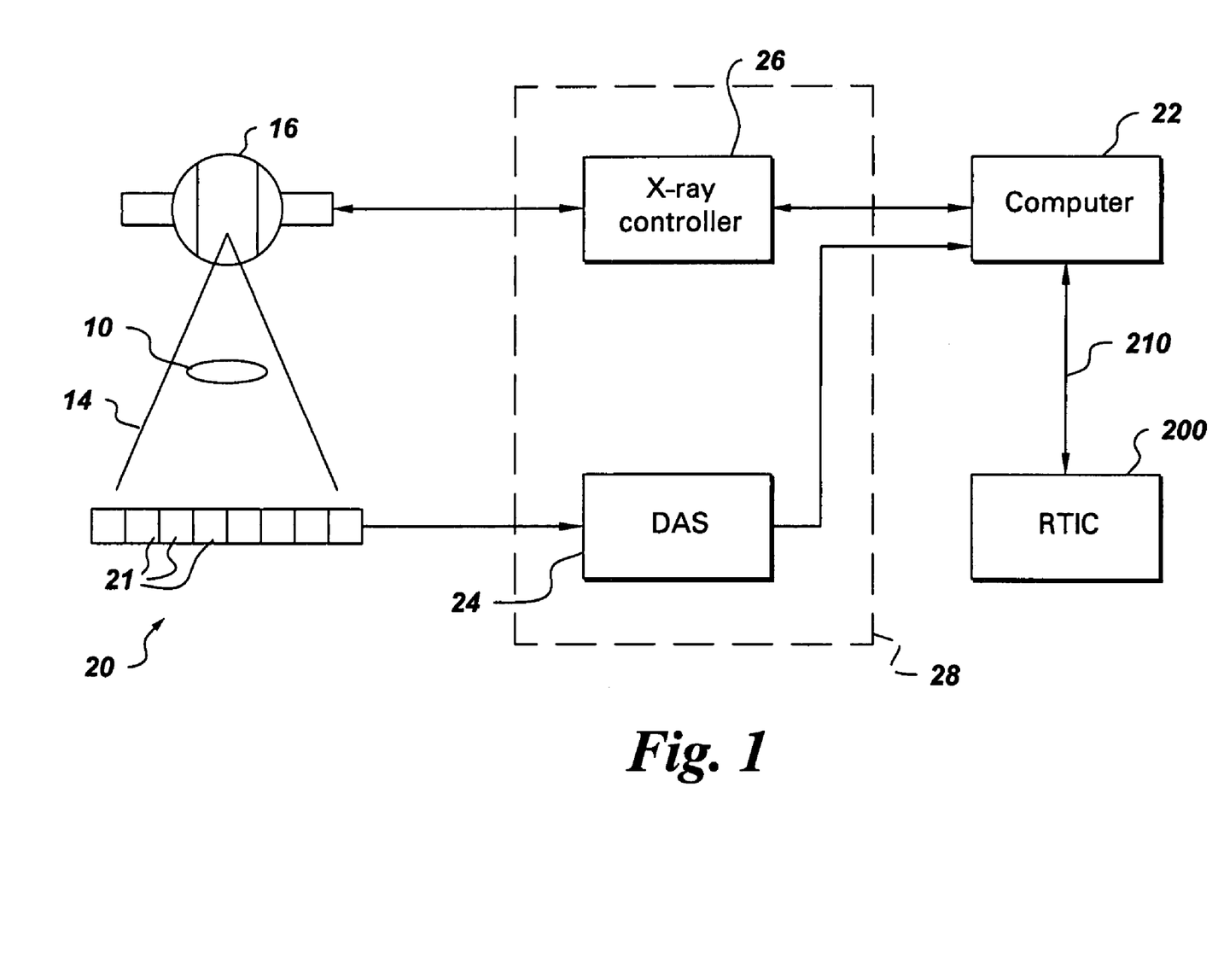
FIG. 1 schematically depicts one embodiment of an energy discrimination radiography system, with source modulation.

Referring to FIG. 1, an energy discrimination radiography system 100 is described. According to one embodiment, energy discrimination radiography system 100 includes at least one radiation source 16 configured to alternately irradiate a component 10 with radiation 14 characterized by at least two energy spectra 30, 32, where the component 10 has a number of constituents 11, 12. Energy discrimination radiography system 100 further includes at least one radiation detector 20 configured to receive radiation 14 passing through component 10, and a computer 22 operationally coupled to the radiation detector 20. Computer 22 is configured to perform the following operations: receive data corresponding to each of the energy spectra for a scan of the component 10, process the data to generate a multi-energy data set, and decompose the multi-energy data set to generate a number of material characterization images 50 in substantially real time.

The invention contemplates other source/detector configurations as well. For example, a geometry system inverse to that of FIG. 1 may be employed, where there is an area source or an array of sources, and a single or reduced-size detector. In another embodiment, a number of sources may be employed, for example two x-ray tubes, operating at different energies, and are switched by gridding or shuttering.

Figure 7:
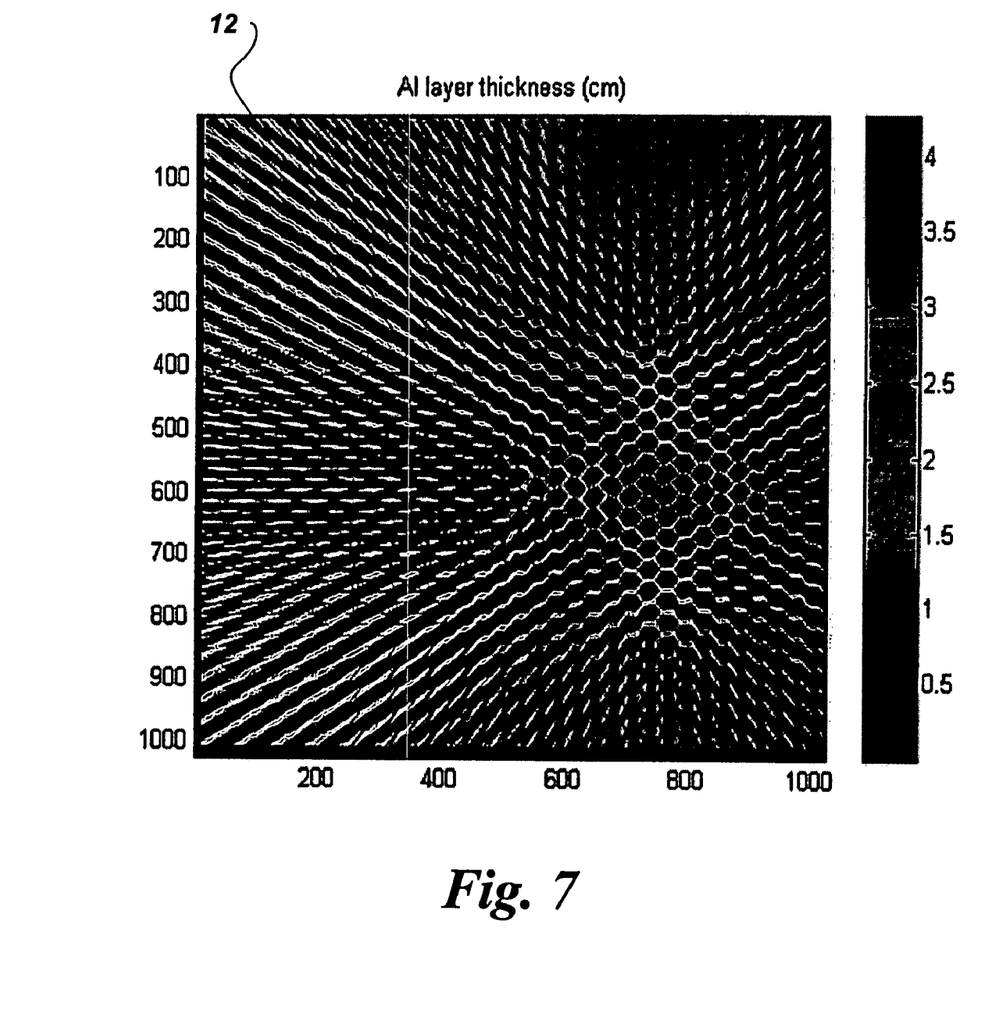
FIG. 7 schematically depicts an exemplary material characterization image for an aluminum honeycomb structure.
Figure 8:
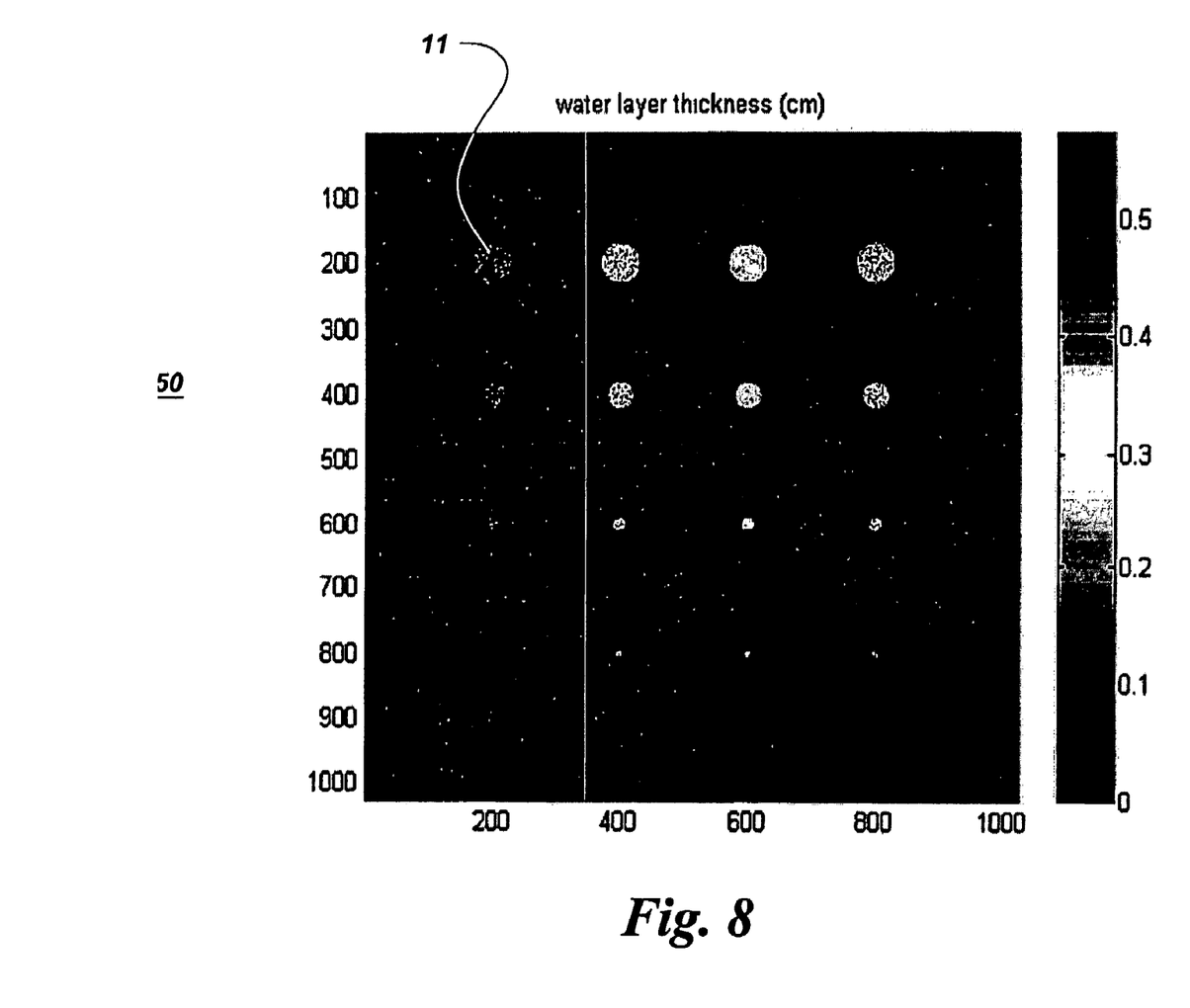
FIG. 8 schematically depicts another exemplary material characterization image for water in the aluminum honeycomb structure.

Exemplary material characterization images 50 are depicted in FIGS. 7 and 8 for an aluminum honeycomb component 10. FIG. 7 shows the aluminum base material, and FIG. 8 shows the water present in the aluminum honeycomb component 10. These images were obtained for 120 kVp and 40 kVp at a ten (10) frame integration.

As used herein, the phrase "substantially real time" refers to material decomposition processes where the material characterization images are generated at or near 30 frames per second. This differs from conventional radiography techniques where a radiography system would collect and store information about the component and finally generate an image at a later time based on the gathered information.

Beneficially, by decomposing the multi-energy data set to generate the material characterization images 50 in substantially real time, the inspection method can be used as a screening process with inspection of a relatively large area occurring in a short time frame. For example, the component 10 can first be inspected at a relatively short exposure. If the constituent of interest, for example corrosion, water or residual ceramic core material, is detected, longer exposure images can then be taken of the particular component 10 or portion of the component 10 (for example a portion of an aircraft fuselage). Generating the material characterization images 50 in substantially real time is critical for the application of this inspection method as a screening process. Similarly, the method can be used in a screening fashion to select the optimal source to detector distances (SDD), viewing angle, region of interest, and exposure, among others. As a result the method provides an improved tool for inspecting complex components.

Another benefit of a real-time energy-discriminating system is the ability to image and decompose materials in a dynamic subject. For example, one could detect the presence and location of small leaks in a metal structure. Imagine a very small leak that results in a small pool of liquid, accumulated somewhere within a structure—the location of the leak may not be where the pool collects. However, with a real time system, one may be able to locate the leak by viewing a droplet that periodically develops on some surface, grows in size, then drips and runs into the pool. Another example is the ability to image moving machinery, and "freeze" movement, where a longer-exposure radiographic system would produce a blurred image. In such a case, one could detect corrosion or leaks in equipment that is in operation, rather than taking it off line for routine inspection.

For the particular embodiment illustrated by FIG. 1, computer 22 is also operationally coupled to radiation source 16. Radiation source 16 projects a beam of x-rays 14 (radiation) toward radiation detector 20 on the other side of the component 10. Exemplary radiation sources 16 include x-ray sources and gamma ray sources. Although many of the embodiments described herein depict x-rays as an exemplary type of radiation for radiographic imaging, it will be appreciated that the disclosed invention is also applicable to other radiation types, such as gamma rays, high-frequency sound waves, magnetic fields, neutrons, or charged particles for example.

The operation of radiation source 16 is governed by a control mechanism 28 of energy discrimination radiography system 100. Control mechanism 28 includes an x-ray controller 26 that provides power and timing signals to radiation source 16. X-ray controller 26 is configured to receive control signals and/or information from computer 22.

There are several ways to generate and detect radiation 14, where energy-dependent (energy discrimination) attenuation measurements are involved. According to one embodiment, radiation source 16 is kVp modulated to generate radiation 14 in at least two spectra. More particularly, radiation source 16 is kVp modulated at a rate of at least about fifteen frames per second (15 fps) and still more particularly, at a rate of at least about thirty frames per second (30 fps). As used herein, the phrase "kVp modulated" refers to kilovolt peak modulation, which involves modulating the potential difference between the anode and the cathode of the radiation source 16. kVp modulation is performed, for example, as follows. Computer 22 sends control signals and/or information to x-ray controller 26 that instruct x-ray controller 26 to modulate the anode-cathode potential of radiation source 16.

Figure 4:
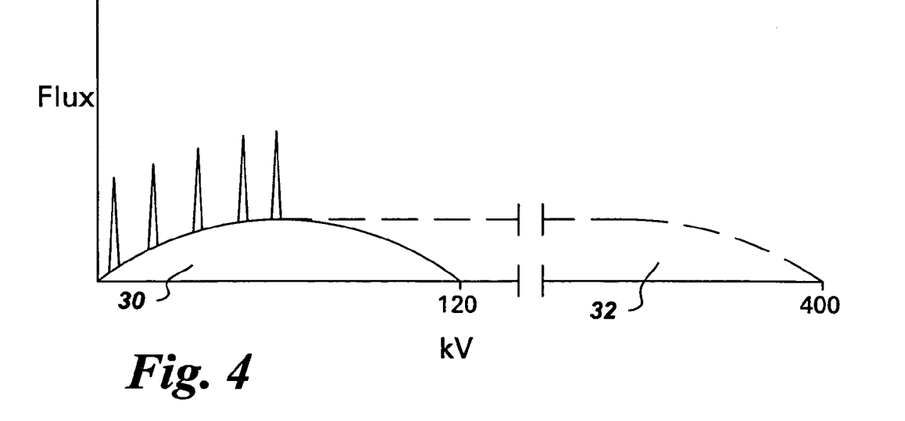
FIG. 4 schematically depicts x-ray flux spectra at two exemplary values of the anode-cathode potential (or kVp)

As is known to those skilled in the art, radiation sources 16 produce radiation 14 characterized by relatively broad energy spectra, as shown for example in FIG. 4. For a given kVp value, such as 120 kV, the radiation produced by radiation source 16 consists of x-rays or gamma rays with energy values in a range of 0–120 keV, which is indicated by reference number 30 in FIG. 4. By changing the kVp value, for example between 120 and 400 kV, radiation source 16 generates radiation 14 in two energy spectra 30, 32, as depicted for example in FIG. 4. Those skilled in the art will recognize that the low and high kVp values shown in FIG. 4, namely 120 and 400 kV, are exemplary. In practice, kVp values are selected (1) to differentiate attenuation at the two energies and (2) for radiation penetration through component 10 in order to achieve good statistical quality for the resulting images or data. More particularly, kVp values are selected based on the material properties (such as density and structure) and dimensions (such as thickness) of the component 10. For example, the kVp values may be selected such that each of the energy spectra 30, 32 corresponds to a respective one of the materials 11, 12 in the component 10. For the exemplary aluminum honeycomb component discussed above with respect to FIGS. 7 and 8, values of 120 kVp and 40 kVp were selected to image the aluminum and water.

It should be noted that although the example shown in FIG. 4 involves two kVp values, kVp modulation can also be performed with three or more kVp values, and the invention encompasses all such embodiments. Moreover, use of the term "alternately irradiate" should not be limited to require any rigid or predefined definition of the modulation sequence (such as low-high-low-high-low-high etc.) Rather, the modulation sequence can take many forms, including for example a random sampling of low and high values. In addition, the term "alternately irradiate" should be understood to include both (1) switching between discrete values of kVp and (2) sweeping between different kVp values.

Radiation detector 20 includes at least one detector row (not shown), which, as indicated in FIG. 1, includes a number of detector elements 21 (or pixels), which together sense the projected x-rays that pass through component 10. Each detector element 21 produces an electrical signal that represents the intensity of an impinging x-ray beam and hence can be used to estimate the attenuation of the beam as it passes through component 10. Accordingly to a particular embodiment, radiation detector 20 includes a number of detector rows arranged in parallel to form a two-dimensional array of detector elements 21. Exemplary radiation detectors 20 include digital x-ray detectors, such as charge integration detectors, examples of which are included in General Electric's Revolution™ digital x-ray detectors. According to one embodiment, radiation detector 20 is an energy discriminating detector, which is described in more detail below. In addition, although conventional digital x-ray detectors are rigid, radiation detector 20 may also be flexibly configured to conform to the component 10. Further, although detector 20 is shown as straight, it may also be curved.

For the exemplary embodiment shown in FIG. 1, energy discrimination radiography system 100 also includes a data acquisition system (DAS) 24 configured to receive data from radiation detector 20. More particularly, DAS 24 samples analog data from detector elements 21 and converts the data to digital signals for subsequent processing.

In one embodiment, computer 22 includes a device, for example, a floppy disk drive, CD-ROM drive, DVD drive, magnetic optical disk (MOD) device (not shown), or any other digital device including a network connecting device such as an Ethernet device (not shown) for reading instructions and/or data from a computer-readable medium, such as a floppy disk, a CD-ROM, a DVD, a MOD or an other digital source such as a network or the Internet, as well as yet to be developed digital means. In another embodiment, computer 22 executes instructions stored in firmware (not shown). Computer 22 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In addition to the data processing functions listed above, computer 22 is configured to provide control signals and/or information to DAS 24 and x-ray controller 26, according to another embodiment.

Nondestructive evaluation of components 10 is performed both in manufacturing and service settings. Depending on the number and identity of the components to be tested, manual or automated inspection processes may be employed. For manual inspection processes or for other inspection processes that are not fully automated, computer 22 may be further configured to receive commands and/or scanning parameters from an operator (not shown) via a console (not shown) that has a keyboard (not shown) either remotely or directly. A display device, such as a cathode ray tube (CRT) display (not shown) allows the operator to observe a reconstructed image and other data from computer 22. The operator supplied commands and parameters are used by computer 22 to provide control signals and information to DAS 24 and x-ray controller 26.

Figure 2:
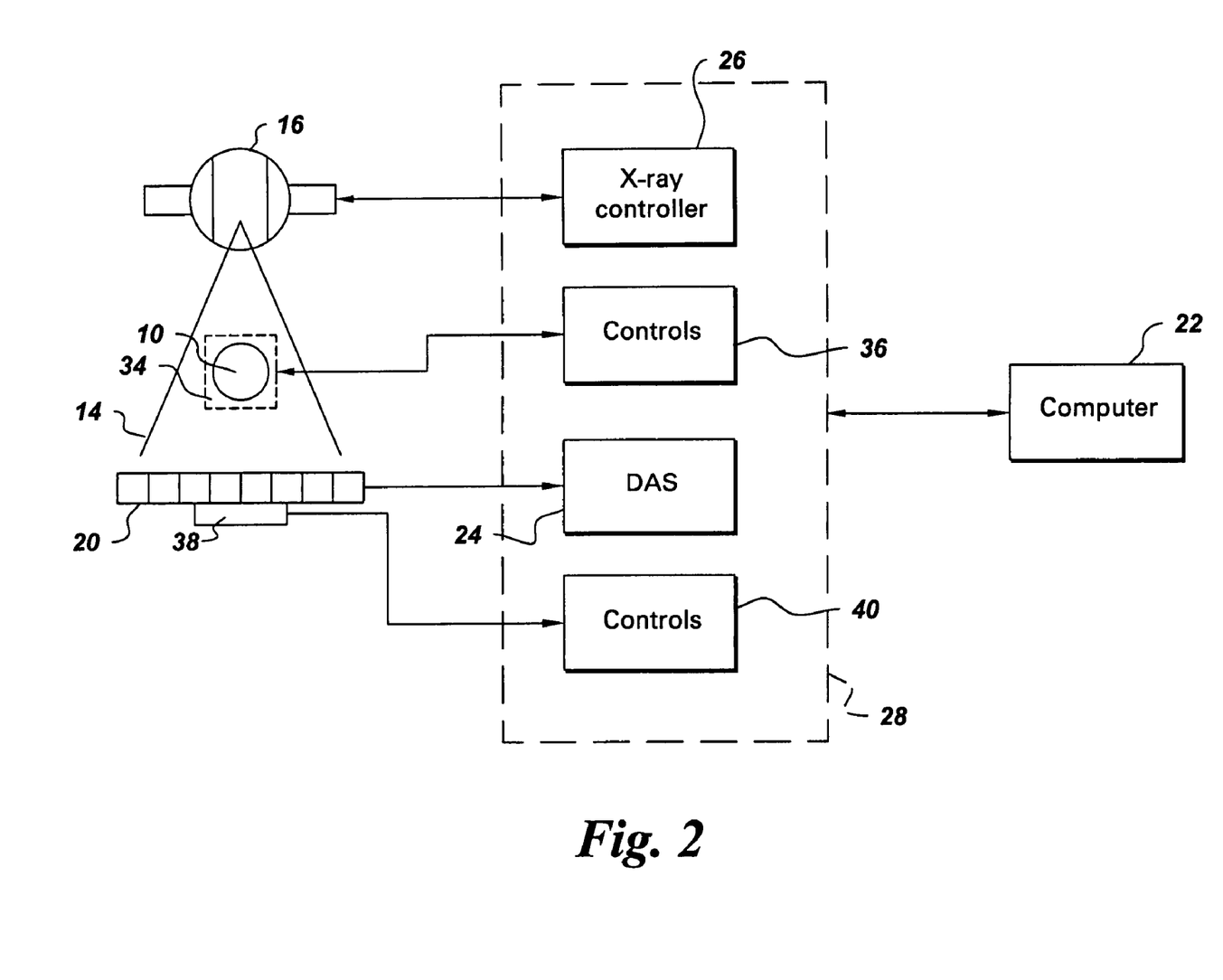
FIG. 2 schematically depicts another embodiment of an energy discrimination radiography system with object and detector manipulation.

For partially or fully automated inspection processes, energy discrimination radiography system 100 may also include a means for positioning the component 10, such as an object manipulator 34. Exemplary object manipulators 34 include a reversible table (not shown) or conveyor belt (not shown) with associated controls 36 for controlling the position of the component 10, as shown schematically in FIG. 2. In addition, energy discrimination radiography system 100 may also include a means for positioning the radiation detector 20, such a set of rails (not shown). The means for positioning the radiation detector 20 may further include an X-Y scanning device or other detector manipulator 38 and associated controls 40, as shown schematically in FIG. 2. For the embodiment of FIG. 2, computer 22 is further configured to communicate with controls 36, 40 to control the positioning of the component 10 and the detector 20. For the embodiment of FIG. 2, controls 36, 40 are part of control mechanism 28.

In addition, energy discrimination radiography system 100 may also include a real-time image controller 200 adapted to be in signal communication with computer 22 via a communication bus 210, as described in commonly assigned, pending U.S. patent application Ser. No. 10/456,280, Bueno et al., filed Jun. 5, 2003 and entitled "Method, System and Apparatus for Processing Radiographic Images of Scanned Objects," which is incorporated by reference herein in its entirety.

As noted above, computer 22 is configured to perform a number of operations including receiving data corresponding to each of the energy spectra for a scan of the component 10. According to one embodiment, the data is x-ray (or other radiation) attenuation data generated by the detector elements 21 that are processed by DAS 24 and communicated to computer 22, which processes the data to generate a multi-energy data set. According to one embodiment, the multi-energy data set is x-ray (or other radiation) attenuation data that correspond to each of the energy spectra. In a particular example, the multi-energy data set is x-ray attenuation data organized into subsets associated with the respective energy spectra, for example, images associated with a high energy spectrum and images associated with a low energy spectrum (multi-energy images). As noted above, computer 22 decomposes the multi-energy data set to generate a number of material characterization images (or basis material images) in substantially real time, which provide information regarding the composition and/or geometry of the component 10.

According to particular embodiments and in order to decompose the multi energy data set, computer 22 is configured to decompose the multi-energy data set using at least one decomposition selected from the group consisting of a Compton and photoelectric decomposition, a basis material decomposition BMD, a logarithm subtraction decomposition LSD, a mean material density and atomic number decomposition, and combinations thereof. In addition, the decomposition may be performed using other suitable decomposition algorithms.

According to a more particular embodiment, computer 22 is further configured to dynamically quantify the constituents 11, 12 of the component 10 based on the material characterization images 50. As used herein, the phrase "dynamically quantify" refers to the quantization of the constituents while the component 10 is in the field of view of ED radiography system 100. For example, when inspecting a portion of an aircraft fuselage (not shown), the dynamic quantification would be performed for a given portion of the fuselage, while that portion of the fuselage remained in the field of view of ED radiography system 100. This differs from conventional systems, which collect and store information while imaging and then quantify materials at a later time. The computer 22 may be configured to quantify the constituents relative to one another and/or absolutely. According to a more particular embodiment, computer 22 is further configured to dynamically locate at least one of the constituents 11, 12 relative to at least one other 12, 11 of the constituents based on the material characterization images. For example, the computer 22 is configured to locate corrosion on a metal part or water in an aluminum honeycomb.

Figure 3:
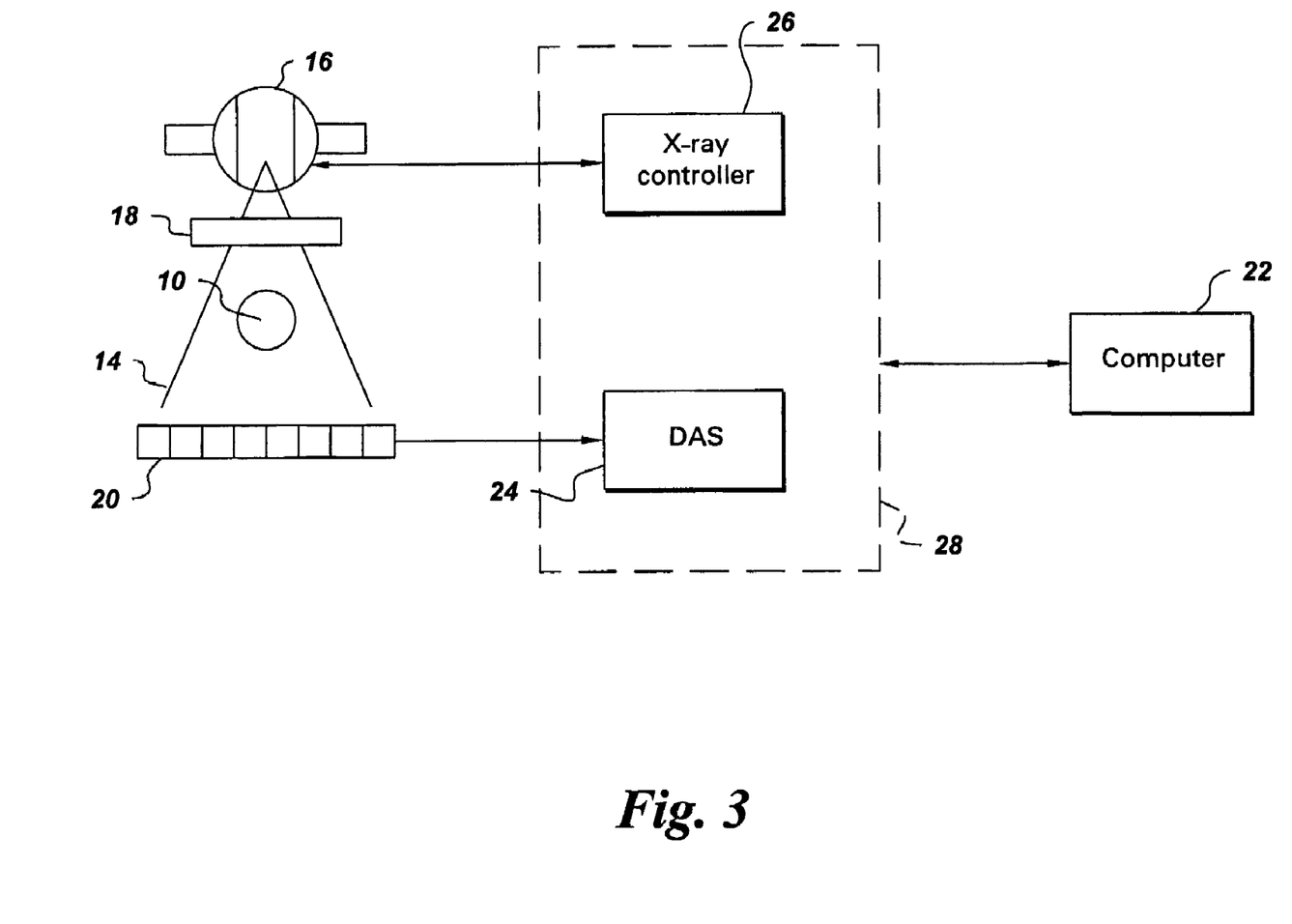
FIG. 3 is a pictorial, view of another embodiment of an energy discrimination radiography system, with source filtering.

Another embodiment is described with reference to FIG. 3. As indicated in FIG. 3, the energy discrimination radiography system 100 includes a filter 18 that is configured to alternately filter the radiation source 16. According to particular embodiments, filter 18 alternately filters radiation source 16 at a rate of at least about fifteen frames per second (15 fps) and, more particularly, at a rate of at least about thirty frames per second (30 fps) to generate radiation 14 in at least two energy spectra. Exemplary filters 18 alternately attenuate the radiation. For example, a single radiation source 16 with a 120 kVp value is filtered by spinning a copper filter with gaps (not shown) to generate broad energy spectrum radiation via the gaps (which includes low energy spectrum radiation) and high energy spectrum radiation via the Copper filter.

In addition to separately employing kVp modulation and source filtering, these two techniques can be combined to generate radiation in two or more energy spectra.

In addition to the embodiments described above, which employ source discrimination, other embodiments of the invention discriminate at the detector in order to accomplish the goals of the invention. An energy discrimination radiography system 100 that energy discriminates at the detector is described with reference to FIGS. 1, 5 and 6. Energy discrimination radiography system 100 includes at least one radiation source 16 configured to irradiate a component 10 having a number of constituents 11, 12. At least one radiation detector 20 is configured to receive radiation passing through the component 10 and to generate a data stream for a scan of the component. The data stream comprises energy discriminated data, specific examples of which are described below. A computer 22 is operationally coupled to radiation detector 20. Computer 22 is configured to perform the following operations: receive the data stream, process the data stream to generate a multi-energy data set, and decompose the multi-energy data set to generate a number of material characterization (basis material) images 50 in substantially real time. The decomposition may be performed using one of the algorithms discussed above or using another suitable decomposition algorithm.

Computer 22 may further be operationally coupled to radiation source 16 as discussed above with respect to FIG. 1. According to a more particular embodiment, computer 22 is further configured to dynamically quantify the constituents 11, 12 of the component 10 based on the material characterization images 50. Dynamic quantification encompasses each of (1) quantifying one of the constituents relative to another of the constituents and (2) absolute quantification, as well as a combination thereof. According to a more particular embodiment, computer 22 is further configured to dynamically locate at least one of the constituents relative to at least one other of the constituents based on the material characterization images 50. For example, computer 22 is configured to locate water in an aluminum honeycomb structure or to locate corrosion on a base metal structure.

As noted above, the multi-energy data set may take the form of multi-energy images. Exemplary material characterization images 50 are shown in FIGS. 7 and 8.

As discussed above, energy discrimination radiography system 100 may further include a data acquisition system (DAS) 24 configured to receive the data stream from radiation detector 20. More particularly, DAS 24 samples analog data from detector elements 21 and converts the data to digital signals for subsequent processing by computer 22. Thus, the data stream generated by radiation detector 20 comprises analog data, whereas the data stream received by computer 22 comprises digital data.

As is known to those skilled in the art, certain data processing steps may be performed in the DAS 24 or in the computer 22, depending on the specific DAS 24 employed. For certain embodiments, such as the energy discriminating detector embodiment described below, DAS 24 is configured to generate at least two data sets from the analog data stream, each of the data sets being characterized by a respective energy spectrum. For these embodiments, the digital data stream received by computer 22 from DAS 24 comprises the data sets, and computer 22 is configured to process the data sets to generate the multi-energy data set, such as multi-energy images. For other embodiments, computer 22 is configured to generate at least two data sets from the digital data stream received from DAS 24, each of the data sets being characterized by a respective energy spectrum, and to process the data sets to generate the multi-energy data set, such as multi-energy images.

Figure 5:
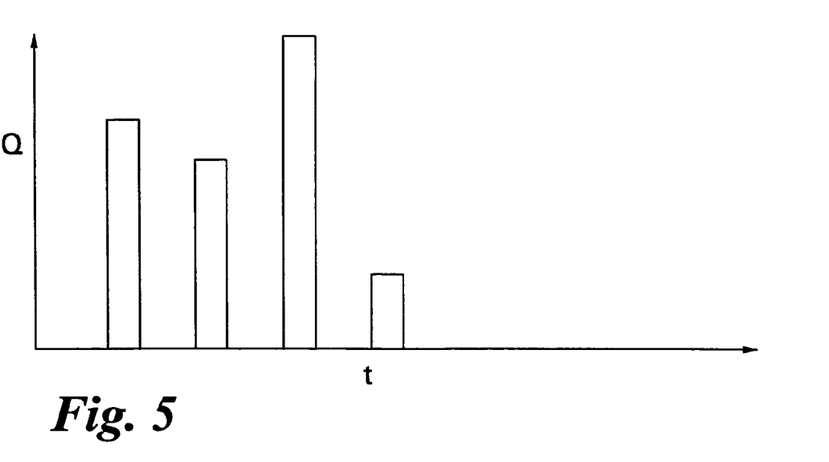
FIG. 5 illustrates the operation of an energy discriminating detector.

For one embodiment, radiation detector 20 is an energy discriminating detector 20. Exemplary energy discriminating detectors include Cadmium Zinc Telluride (CZT) direct conversion detectors and high speed scintillators with avalanche photodiodes. As indicated in FIG. 5, energy discriminating detector 20 generates a stream of energy discriminated data comprising waveforms (or pulses) the shape of which depends upon the incident x-ray photon energy. For this embodiment, DAS 24 converts the data stream to digital data and may additionally perform certain signal processing, such as converting pulse height to x-ray energy. Computer 22 receives the digital, energy-discriminated data stream from DAS 24 (for example in the form of at least two data sets, each corresponding to a different energy spectrum) and processes the data sets to generate a multi-energy data set, which is then decomposed to generate a number of material characterization images 50.

Figure 6:
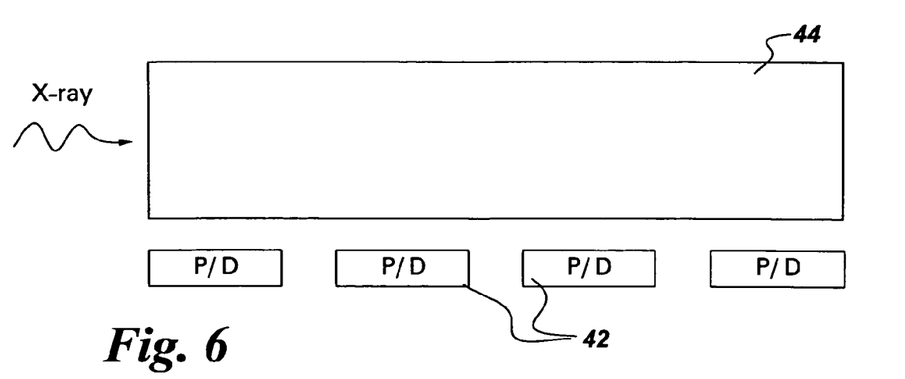
FIG. 6 schematically depicts an exemplary multilayer detector.

According to another embodiment, radiation detector 20 is a multilayer charge integration detector 20, one example of which is illustrated simplistically in FIG. 6. As is known to those skilled in the art, low energy radiation is more readily absorbed than is higher energy radiation. Consequently, the detector 20 depicted in FIG. 6 effectively forms a multilayer structure, within which each of the photodetectors 42 and the corresponding scintillator 44 portion measure x-ray absorption. From this data, the x-ray absorption in different energy spectra can be determined. For a multilayer charge integration detector 20, each of the photodetectors 42 and associated electronics are configured as a charge integration detector.

For another embodiment, radiation detector 20 is a multilayer photon counting detector 20. This embodiment is also illustrated by FIG. 6. For this embodiment, each of the photodetectors 42 and associated electronics are configured as a photon counting detector.

According to a more particular embodiment and in order to create multi-energy images at real time rates, radiation detector 20 is configured to generate a data stream at a rate of at least about 500 kHz, and more particularly, at a rate of at least about 1 MHz.

In addition to separately employing energy discrimination at the source and energy discrimination at the detector, these two techniques can be combined to generate radiographic data corresponding to two or more energy spectra.

A method for inspecting a component 10 having a number of constituents 11, 12 is described with reference to FIG. 1. The method includes alternately irradiating the component with radiation 14 characterized by at least two energy spectra 30, 32 to scan the component. A first one of the energy spectra is different than a second one of the energy spectra, for example as exemplarily shown in FIG. 4. As discussed above, the different energy spectra may be selected to target the constituents of the component. The method further includes receiving data corresponding to each of the energy spectra, processing the data to generate a multi-energy data set, and decomposing the multi-energy data set to generate a number of material characterization images 50 in substantially real time. The decomposition may be performed using one of the algorithms discussed above or using another suitable decomposition algorithm.

As noted above, the multi-energy data set may take the form of multi-energy images. According to particular embodiments, each of the material characterization images 50 corresponds to a respective one of the constituents 11, 12 of the component 10, as illustrated for example in FIGS. 7 and 8, which depict an aluminum honeycomb structure and water in the honeycomb structure.

There are several ways to generate radiation 14 in at least two energy spectra. According to one embodiment, the step of alternately irradiating involves kVp modulating radiation source 16, as discussed above with respect to FIG. 4. Exemplary kVp modulation rates include at least fifteen frames per second (15 fps) and at least thirty frames per second (30 fps). Moreover, although the example shown in FIG. 4 involves two kVp values, kVp modulation can also be performed with three or more kVp values, and the invention encompasses all such embodiments. Moreover, use of the term "alternately irradiate" should not be limited to require any rigid or predefined definition of the modulation sequence (such as low-high-low-high-low high etc). Rather, the modulation sequence can take many forms, including for example a random sampling of low and high values. In addition, the term "alternately irradiate" should be understood to include both (1) switching between discrete values of kVp and (2) sweeping between different kVp values.

Another embodiment is described with reference to FIG. 3. For this embodiment, the step of alternately irradiating involves filtering radiation source 16, and exemplary filtering rates include at least about fifteen frames per second (15 fps) and at least about thirty frames per second (30 fps).

Moreover, in addition to separately employing kVp modulation and source filtering, the step of alternately irradiating may include performing both kVp modulation and source filtering to generate radiation in two or more energy spectra.

According to a particular embodiment, the method further includes dynamically quantifying the constituents 11, 12 of the component 10 based on the material characterization images 50. As discussed above, the constituents 11, 12 may be dynamically quantified by determining an amount of one of the constituents 11, 12 relative to another of the constituents 12, 11. In addition, the constituents 11, 12 may be dynamically quantified by determining an absolute amount of at least one of the constituents 11, 12. These relative and absolute quantification techniques can be employed separately and in combination.

In addition to quantifying the basis materials 11, 12 of the component 10, it is desirable to determine the location of one or more constituents in the structure during imaging. Accordingly, the method further includes dynamically locating at least one of the constituents 11, 12 relative to another of the constituents 12, 11 based on the material characterization images 50, in a particular embodiment. As used herein the phrase "dynamically locating" refers to the location of the constituents while the component 10 is in the field of view of the radiography system. For example, when inspecting a portion of an aircraft fuselage (not shown), the dynamic location would be performed for a given portion of the fuselage, while the portion of the fuselage being imaged remained in the field of view of the radiography system. This differs from conventional radiographic inspection methods, which collect and store information while imaging and then process the data at a later time. Beneficially, dynamically locating the constituents 11, 12 permits the user to assess the structure's condition in substantially real time as a screening process and to select and obtain longer exposure images based on the results of the screening process.

A few example applications of these techniques are described. In one example, one of the constituents 11, 12 is water, and another of the constituents 12, 11 is a base material, such as a metal. For this example, the material characterization images 50 would include at least one image of the water in the component 10 and at least one image of the base material. For the example illustrated by FIGS. 7 and 8, the base material forms a honeycomb structure, and the inspection method is used to dynamically locate and quantify the water in the honeycomb structure. In another example, one of the constituents 11, 12 is corrosion and another of the constituents 12, 11 is a base material, such as a metal. For this example, the material characterization images 50 include at least one image of the corrosion in the component 10 and at least one image of the base material.

For another example, one of the constituents is residual ceramic core remaining in the component 10 after a casting process and another of the constituents is a cast material. For this example, the material characterization images 50 include at least one image 50 of the residual ceramic core in the component 10 and at least one image 50 of the cast material. For this example, the method includes dynamically locating and quantifying the residual ceramic core in the cast material.

As discussed above, the inventive method can beneficially be used as a screening process. For a particular embodiment, the method further includes optimizing at least one viewing angle based on the material characterization images 50. For example, the method may be used to inspect the component 10 and if the material characterization images 50 indicate the presence of a constituent of interest, such as corrosion, the viewing angle may be modified to improve the inspection of the component or of the portion of the component being imaged. Similarly, the method may further include selecting the optimal source to detector distances (SDD), region of interest, and radiation exposure based upon the material characterization images 50. As used herein, the viewing angle should be understood to mean the relative orientation of the source, detector and object.

Another method for inspecting component 10 is described with reference to FIGS. 1, 5 and 6. The method includes irradiating the component 10 and receiving a data stream corresponding to radiation passing through component 10, the data stream comprising energy discriminated data. The method further includes generating at least two data sets, each of the data sets being characterized by a respective energy spectrum, processing the data sets to generate a multi-energy data set, and decomposing the multi-energy data set to generate a number of material characterization images 50 in substantially real time. The decomposition may be performed using one of the algorithms discussed above or using another suitable decomposition algorithm. Moreover, as noted above, the multi-energy data set may take the form of multi-energy images. According to particular embodiments, the data stream is received from an energy discriminating detector, from a multilayer charge integration detector or from a multilayer photon counting detector. According to a more particular embodiment, the data stream is received at a rate of at least about 500 kHz, and more particularly at a rate of about 1 MHz.

According to a more particular embodiment, the method further includes dynamically quantifying the constituents 11, 12 of the component 10 based on the material characterization images 50. The constituents can be quantified relative to one another, absolutely or both. In another embodiment, the method further includes dynamically locating at least one of the constituents relative to another of the constituents based on the material characterization images 50. Beneficially, the method may be used as a screening process and may further include the following operations to better inspect component 10: optimizing at least one viewing angle based on the material characterization images, modifying a source to detector distance based on the material characterization images, selecting a region of interest based on the material characterization images and/or changing a radiation exposure level based on the material characterization images. By generating material characterization images 50 in substantially real time, these and other adjustments can be made during the inspection process, resulting in improved imaging of complex components, including components with minor corrosion.

Although only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for inspecting a component comprising a plurality of constituents, said method comprising:
    alternately irradiating the component with radiation characterized by at least two energy spectra to scan the component, wherein a first one of the energy spectra is different than a second one of the energy spectra;
    receiving data corresponding to each of the energy spectra;
    processing the data to generate a multi-energy data set;
    decomposing the multi-energy data set to generate a plurality of material characterization images in substantially real time; and
    dynamically quantifying in a computer the constituents of the component based on the material characterization images, and generating a corresponding signal.

2. The method of claim 1, wherein the multi-energy data set comprises a plurality of multi-energy images.

3. The method of claim 1, wherein each of the material characterization images corresponds to a respective one of the constituents of the component.

4. The method of claim 1, wherein said step of alternately irradiating comprises kVp modulating at least one radiation source at a rate of at least about fifteen frames per second (15 fps).

5. The method of claim 1, wherein said alternately irradiating comprises filtering at least one radiation source at a rate of at least about fifteen frames per second (15 fps).

6. The method of claim 1, wherein said step of dynamically quantifying the constituents comprises determining an amount of one of the constituents relative to another of the constituents.

7. The method of claim 6, wherein said step of dynamically quantifying the constituents further comprises determining an absolute amount of at least one of the constituents.

8. The method of claim 1, wherein said step of dynamically quantifying the constituents comprises determining an absolute amount of at least one of the constituents.

9. The method of claim 1, further comprising:
dynamically locating at least one of the constituents relative to at least one other of the constituents based on the material characterization images.

10. The method of claim 9, wherein one of the constituents comprises water and another of the constituents comprises a base material, wherein the material characterization images comprise at least one image of the water in the component and at least one image of the base material.

11. The method of claim 10, wherein the base material forms a honeycomb structure, and wherein said steps of dynamically locating and quantifying the water and the base material comprise dynamically locating and quantifying the water in the honeycomb structure.

12. The method of claim 9, wherein one of the constituents comprises corrosion and another of the constituents comprises a base material, wherein the material characterization images comprise at least one image of the corrosion in the component and at least one image of the base material.

13. The method of claim 9, wherein one of the constituents comprises residual ceramic core and another of the constituents comprises a cast material, wherein the material characterization images comprise at least one image of the residual ceramic core in the component and at least one image of the cast material, and wherein said steps of dynamically locating and quantifying the residual ceramic core and the cast material comprise dynamically locating and quantifying the residual ceramic core in the cast material.

14. The method of claim 1, further comprising
optimizing at least one viewing angle based on the material characterization images.

15. The method of claim 1, further comprising
modifying a source to detector distance based on the material characterization images.

16. The method of claim 1, further comprising selecting a region of interest based on the material characterization images.

17. The method of claim 1, further comprising
changing a radiation exposure level based on the material characterization images.

18. A method for inspecting a component comprising a plurality of constituents, said method comprising:
irradiating the component;
receiving a data stream corresponding to radiation passing through the component, the data comprising energy discriminated data;
processing the energy discriminated data to generate a multi-energy data set;
decomposing the multi-energy data set, to generate a plurality of material characterization images in substantially real time; and
dynamically quantifying in a computer, the constituents of the component based on the material characterization images, and generating a corresponding signal.

19. The method of claim 18, wherein the data stream is received from a detector selected from the group consisting of an energy discriminating detector, a multilayer charge integration detector and a multilayer photon counting detector, and wherein the data stream is received at a rate of at least about 500 kHz.

20. The method of claim 18, further comprising:
dynamically locating at least one of the constituents relative to at least one other of the constituents based on the material characterization images,
wherein one of the constituents comprises corrosion and another of the constituents comprises a base material, and wherein the material characterization images comprise at least one image of the corrosion in the component and at least one image of the base material.

21. The method of claim 18, further comprising:
performing at least one of the following operations:
optimizing at least one viewing angle based on the material characterization images,
modifying a source to detector distance based on the material characterization images,
selecting a region of interest based on the material characterization images, and
changing a radiation exposure level based on the material characterization images.

22. An energy discrimination radiography system comprising:
at least one radiation source configured to alternately irradiate a component with radiation characterized by at least two energy spectra, wherein the component comprises a plurality of constituents;
at least one radiation detector configured to receive radiation passing through the component; and
a computer operationally coupled to said at least one radiation detector, said computer being configured to:
receive data corresponding to each of the energy spectra for a scan of the component;
process the data to generate a multi-energy data set;
decompose the multi-energy data set to generate a plurality of material characterization images in substantially real time; and
dynamically quantify the constituents of the component based on the material characterization images.

23. The energy discrimination radiography system of claim 22, wherein said at least one radiation source is kVp modulated to generate radiation in at least two spectra, and wherein said radiation detector is selected from the group consisting of a digital radiation detector and an energy discriminating detector.

24. The energy discrimination radiography system of claim 22, further comprising a filter configured to alternately filter said at least one radiation source to generate radiation in at least two energy spectra, and wherein said radiation detector is selected from the group consisting of a digital radiation detector and an energy discriminating detector.

25. The energy discrimination radiography system of claim 22, wherein said computer is further configured to:
dynamically locate at least one of the constituents relative to at least one other of the constituents based on the material characterization images.

26. An energy discrimination radiography system comprising:
at least one radiation source configured to irradiate a component comprising a plurality of constituents;
at least one radiation detector configured to receive radiation passing through the component and to generate a data stream for a scan of the component, the data stream comprising energy discriminated data; and
a computer operationally coupled to said at least one radiation detector, said computer being configured to:
receive the data stream;
process the data stream to generate a multi-energy data set;

decompose the multi-energy data set to generate a plurality of material characterization images in substantially real; and dynamically quantify the constituents of the component based on the material characterization images.

27. The energy discrimination radiography system of claim 26, wherein the multi-energy data set comprises at least one multi-energy image.

28. The energy discrimination radiography system of claim 26, wherein said radiation detector is selected from the group consisting of an energy discriminating detector, a multilayer charge integration detector and a multilayer photon counting detector.

29. The energy discrimination radiography system of claim 26, wherein said computer is further configured to:

dynamically locate at least one of the constituents relative to at least one other of the constituents based on the material characterization images.

* * * * *